United States Patent [19]

Takahashi et al.

[11] 3,968,240
[45] July 6, 1976

[54] α-CHLORO-O-ACYLBENZALDOXIME DERIVATIVES AS SLIME CONTROL AGENTS

[75] Inventors: Nobuyasu Takahashi, Koshigaya; Taiichi Yamaguchi, Kasuhabe; Junei Sakaguchi, Kawasaki; Hideo Hamada, Soka, all of Japan

[73] Assignee: Somar Manufacturing Co., Ltd., Tokyo, Japan

[22] Filed: May 21, 1975

[21] Appl. No.: 579,744

Related U.S. Application Data

[63] Continuation-in-part of Ser. No. 341,651, March 15, 1973, abandoned.

[30] Foreign Application Priority Data

Mar. 16, 1972 Japan.............................. 47-26748

[52] U.S. Cl................................ 424/311; 424/298; 424/327
[51] Int. Cl.²........................................... A01N 9/24
[58] Field of Search.................... 424/298, 311, 327; 260/566 AE

[56] References Cited
UNITED STATES PATENTS 3,655,761  4/1972  Gutman ............................. 424/327
3,742,036  6/1973  Perronnet et al. ............... 424/314 X
3,843,724  10/1974  Gatzi................................. 424/327 X
3,885,043  5/1975  Baker et al. ......................... 424/327

FOREIGN PATENTS OR APPLICATIONS 6,906,556  5/1970  Netherlands........................ 424/327
951,449  3/1964  United Kingdom
238,537  7/1969  U.S.S.R.

OTHER PUBLICATIONS

J. Am. C. S., vol. 79, 462, (1957).
Chem. Abst.; vol. 66, (1967), 56, 916h.

Primary Examiner—Jerome D. Goldberg
Assistant Examiner—Allen J. Robinson
Attorney, Agent, or Firm—Sughrue, Rothwell, Mion, Zinn & Macpeak

[57] ABSTRACT

A composition containing an α-chloro-o-acylbenzaldoxime derivative is effective for inhibiting the formation of slime. The composition has a strong activity for killing microorganisms which form slime, e.g., in the paper and pulp industries without such faults as reducing the whiteness of the paper or pulp, reducing the effect of sizing treatments, degrading the products, etc. A method for controlling slime using this composition is also disclosed.

26 Claims, No Drawings

α-CHLORO-O-ACYLBENZALDOXIME DERIVATIVES AS SLIME CONTROL AGENTS

CROSS-REFERENCE TO RELATED APPLICATION

This application is a continuation-in-part application of Ser. No. 341,651, filed Mar. 15, 1973, now abandoned.

BACKGROUND OF THE INVENTION

1. Field of the Invention

The present invention relates to slime control agents especially useful in the paper and pulp industries, more particularly it relates to a slime inhibitor containing as the effective component at least one α-chloro-o-acylbenzaldoxime derivative represented by the following general formula

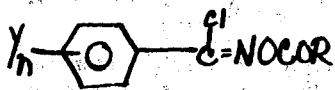

wherein Y represents a halogen atom, a nitro group, a lower alkyl group, a lower alkoxyl group, a lower alkylcarboxy group, or a lower alkylamino group; R represents lower alkyl group or a halogenated alkyl group; and n represents 0 or an integer of 1-3.

The invention further relates to a slime control composition containing the aforesaid α-chloro-o-acylbenzaldoxime derivative and a known slime control agent such as a halogenated phenol or methylene bisthiocyanate as effective components, and also relates to a method of controlling slime using all such compositions.

2. Description of the Prior Art

In paper manufacturing, microorganisms are apt to generate quite easily in various processing streams. In such a case it sometimes happens that the microorganisms and the secretions thereof form a viscous material called slime on chests, pipes, and the like during the manufacture of paper. The generation of such slime is accompanied by a reduction in working efficiency, tearing of paper and the formation of stains in products, and thus causes a great amount of trouble in the production of paper and pulp. Therefore, the occurence of slime must be prevented in the manufacture of paper and pulp and it is necessary to kill the slime-forming microorganisms and to restrain the generation of such microorganisms during the manufacture of paper or pulp.

As is well known to those skilled in the art, the slime produced in the paper mill is a viscous mass having various forms and appearances such as a soft paste-like, gelatinous, gummy, fibrous, hard or horny mass which emits unpleasant odors. In many cases, the slime is a colored amorphous mass and is generally composed of heterogeneous materials, i.e., microorganisms, such as bacteria, fungi, yeast and algae and the metabolites thereof, pulp fibers and various additives incorporated into the pulp stream. The problems caused by slime are usually due to a mass as described above and are not serious if the heterogeneous materials are present in the discrete state even though the materials are contained in a relatively large amount in the pulp. A mass of slime is considered to be formed by growing viscous masses as nuclei produced by pulp fibers, additives, microorganisms and the like where the inner wall of paper mill system is rough and where the flow stream of the pulp or pulp suspension stagnates. The microorganisms, main source of the slime, are usually borne by industrial water consumed in a large quantity and raw pulp woods into paper processing systems. Additionally, since most paper processing steps are conducted while being exposed to air, there is the possibility that the pulp will be contaminated with various microorganisms floating in the air. Once the pulp is contaminated with the microorganisms, they usually grow abundantly in the raw pulp since the raw pulp and the white liquor can offer optimum conditions for microorganism growth in view of their nutrients, moisture, temperature, pH and oxygen supply. The slime formed in the paper mill systems causes various colored spots or stains in the paper product and may be the main factor in a decrease in strength and an increase in breaking of the paper product.

The slime also causes contamination and/or clogging of wires and felts used in paper processing and adversely affects the durability of such equipment due to deterioration of the material of the equipment. Thus, the operation of pulp and paper processings must be discontinued for cleaning, thereby decreasing the production efficiency and causing damage to the raw pulp materials.

It is advantageous to control or kill microorganisms having a tendency to produce such slime by a chemical treatment, i.e., by incorporating various slime controlling agents into the process streams. Slime is generally produced by various microorganisms such as bacteria, fungi, yeast and the like, so it is usually necessary to use different types of slime controlling agents at the same time. In light of the above, it would be a great advantage in the art if various microorganisms grown in the process streams in a paper mill could be controlled by a single chemical agent.

The slime controlling agents which have conventionally been used are organometallic compounds, chlorinated phenols and dithiocarbamate derivatives. These well known compounds are not satisfactory because they are toxic to humans, emit an unpleasant odor per se or even in the paper products, lower the whiteness of the paper, decrease the sizing efficiency, etc.

SUMMARY OF THE INVENTION

One object of this invention is, therefore, to provide an effective slime control agent for the paper and pulp manufacturing industries.

Another object of this invention is to provide a composition capable of effectively killing microorganisms forming slime and also restraining the generation of such microorganisms during the manufacture of paper and pulp.

A further object is to provide a method of controlling slime using such agents and compositions.

As the result of various investigations to discover chemicals capable of killing or controlling microorganisms forming slime in the manufacture of paper and pulp, the inventors discovered that the α-chloro-o-acylbenzaldoxime derivatives represented by the following general formula have a strong activity on various microroganisms with an improved spectrum of activity. The compositions comprising α-chloro-o-acylbenzaldoxime derivatives as main components are excellent slime controlling agents in the paper mill without having the disadvantages encountered in conventional slime controlling agents.

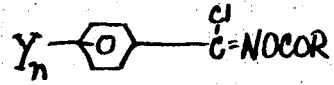

wherein Y represents a halogen atom, a lower alkyl group, a lower alkoxyl group, a lower alkylcarboxy group, or a lower alkylamino group; R represents a lower alkyl group or a halogenated alkyl group; and $n$ represents O or an integer of 1–3.

More particularly, the present invention is directed to a slime control composition for paper and pulp manufacturing comprising an organic solvent and as an effective component in said composition, about 2.5 to about 40 parts/million of an α-chloro-o-acylbenzaldoxime derivative represented by the formula:

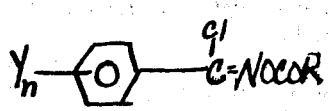

wherein Y represents a chlorine atom, a nitro group, a methyl group, an isopropyl group, a methoxy group, a dimethylamino group, a propionyloxy group or an acetoxy group, and R represents a methyl group, an ethyl group, or a monochloromethyl group, and $n$ is as defined above.

While the present invention is described primarily in terms of the paper and pulp industries, it will be apparent to one skilled in the art that the present invention will find application in any industry where a similar slime problem is encountered under similar conditions.

DETAILED DESCRIPTION OF THE INVENTION.

It has been discovered that the compositions of this invention which contain as the effective component at least one α-chloro-o-acylbenzaldoxime derivative indicated by the above formula show a strong and wide fungicidal activity against slime generating microorganisms as are encountered in the paper and pulp industry without undesirable side effects such as lowering product quality e.g., reducing whiteness, harming sizing or generating bad odors, and the composition does not harm the working environment and has a low corrosive action due to the low vapor pressure of the derivatives and, thus, the composition is quite suitable as a slime inhibitor or slime controlling agent in the paper and pulp manufacturing industries.

Preferred α-chloro-o-acylbenzaldoxime derivatives are those represented by the formula

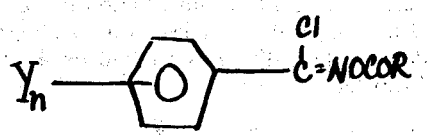

wherein Y represents a halogen atom such as chlorine, bromine, iodine and fluorine, preferably chlorine and bromine, a lower alkyl group having 1 to 8 carbon atoms, preferably 1 to 3 carbon atoms, a lower alkoxy group, a lower alkylcarboxy group or a lower alkylamino group wherein the lower alkyl moiety has 1 to 8 carbon atoms, preferably 1 to 3 carbon atoms; and R represents a lower alkyl group having 1 to 8 carbon atoms, preferably 1 to 3 carbon atoms, or a halogenated alkyl group having 1 to 8 carbon atoms, preferably 1 to 3 carbon atoms, wherein the halogen is chlorine, bromine, iodine or fluorine, preferably chlorine or bromine, and $n$ represents O or an integer of 1–3.

Typical examples of the α-chloro-o-acylbenzaldoxime derivatives of this invention will be illustrated below together with the physical properties thereof:

1. α-Chloro-o-acetylbenzaldoxime

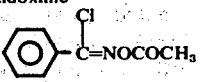

m. p. 43–45°C.    white solid,

2. α-Chloro-o-propionylbenzaldoxime

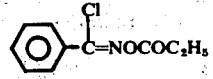

m. p. 52–53°C.    white solid,

3. α-Chloro-o-chloroacetylbenzaldoxime

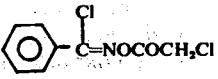

m. p. 56°C.    white solid,

4. α-Chloro-o-acetyl-2-chlorobenzaldoxime

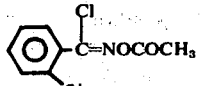

m. p. 45–47°C.    white solid,

5. α-Chloro-o-propionyl-2-chlorobenzaldoxime

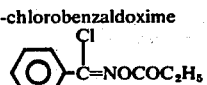

m. p. 48–50°C.    white solid,

6. α-Chloro-o-chloroacetyl-2-chlorobenzaldoxime

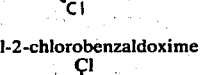

m. p. 58–60°C.    white solid,

7. α-Chloro-o-acetyl-4-chlorobenzaldoxime

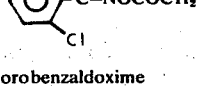

m. p. 75–76°C.    white solid,

8. α-Chloro-o-acetyl-2,4-dichlorobenzaldoxime

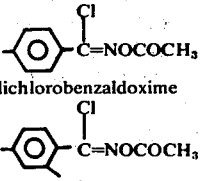

m. p. 103–104°C.    white solid,

-continued

9. α-Chloro-o-acetyl-2,6-dichlorobenzaldoxime

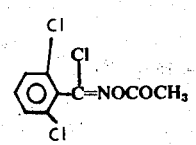

m. p. 106°C.    white solid,

10. α-Chloro-o-acetyl-3-nitrobenzaldoxime

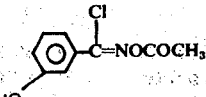

m. p. 71–72°C.    white solid,

11. α-Chloro-o-propionyl-3-nitrobenzaldoxime

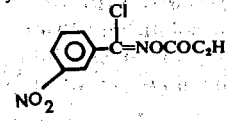

m. p. 51–53°C.    white solid,

12. α-Chloro-o-chloroacetyl-3-nitrobenzaldoxime

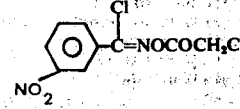

m. p. 53–55°C.    white solid,

13. α-Chloro-o-acetyl-4-methylbenzaldoxime

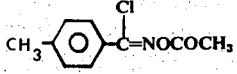

m. p. 73–74°C.    white solid,

14. α-Chloro-o-propionyl-4-methylbenzaldoxime

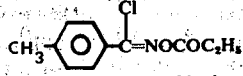

b. p. 118–120°C/10 mm.    faint-yellow liquid,

15. α-Chloro-o-chloroacetyl-4-methylbenzaldoxime

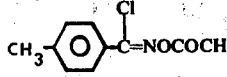

m. p. 32–33°C.    white solid,

16. α-Chloro-o-acetyl-4-isopropylbenzaldoxime

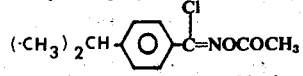

b. p. 125–130°C./10 mm.    faint-yellow liquid,

17. α-Chloro-o-propionyl-4-isopropylbenzaldoxime

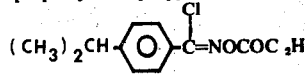

b. p. 155–160°C./10 mm.    faint-yellow liquid,

18. α-Chloro-o-acetyl-4-methoxybenzaldoxime

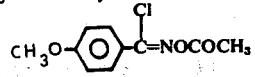

m. p. 78–79°C.    white solid,

19. α-Chloro-o-propionyl-4-methoxybenzaldoxime

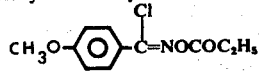

m. p. 45–48°C.    white solid,

20. α-Chloro-o-acetyl-4-acetoxy-3,5-dibromobenzaldoxime

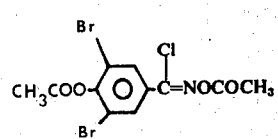

m. p. 89–93°C.    white solid,

21. α-Chloro-o-propionyl-4-propionyloxy-3,5-dibrombenzaldoxime

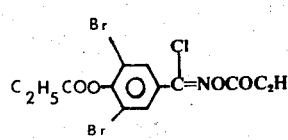

m. p. 98–102°C.    white solid,

22. α-Chloro-o-acetyl-4-dimethylaminobenzaldoxime

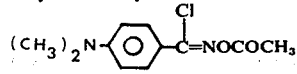

m. p. 165–167°C.   white solid,

23. α-Chloro-o-propionyl-4-dimethylaminobenzaldoxime

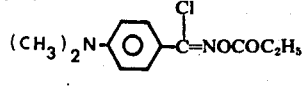

m. p. 172–175°C.   white solid,

The concentrations of the compounds of this invention for completely checking the growth of the microorganisms are shown in the following table. The bacteria or fungi used in the test were typical ones separated from slime generated on the chest, decker machines, rifflar, etc., in paper manufacturing steps in Japan.

The culture medium used was an aqueous solution containing 0.1% peptone, 0.05% dextrose, 0.01% sodium phosphate and 0.005% magnesium sulfate.

Each of the test microorganisms listed below was suspended in a controlled culture medium, and an aliquot of each suspension was placed in a clean test tube. To the test tube there was added each of the compounds of this invention at concentrations of 2.5, 5, 10, 20, 40, 60 and 80 ppm and the microorganisms were shake-cultured at a temperature of 32°C. After 24 hours cultivation, the growth of the microorganisms in each test tube was rated by observing the degree of turbidity of the resulting culture solution due to the propagation of the microorganisms. The concentration at which the growth of the microorganism was completely inhibited (the culture solution showing no turbidity) was referred to as the minimum inhibitory concentration. The results obtained are shown in Table below.

| Name of the microoganisms: | Abbreviation |
|---|---|
| Aerobacter aerogenes | A.a. |
| Bacillus subtilis | B.s. |
| Alcaligenes viscosus | A.v. |
| Aspergillus niger | A.n. |
| Yeast | Y. |

| Compound | | Minimum Inhibitory Concentration (p.p.m.) Microorganisms | | | | |
|---|---|---|---|---|---|---|
| | | A.a | B.s. | A.v. | A.n. | Y. |
| 1. | ⟨O⟩–C(Cl)=NOCOCH₃ | 2.5 | 2.5 | 2.5 | 2.5 | 2.5 |
| 2. | ⟨O⟩–C(Cl)=NOCOC₂H₅ | 2.5 | 2.5 | 2.5 | 2.5 | 2.5 |
| 3. | ⟨O⟩–C(Cl)=NOCOCH₂Cl | 2.5 | 2.5 | 2.5 | 2.5 | 2.5 |
| 4. | ⟨O⟩(Cl)–C(Cl)=NOCOCH₃ | 2.5 | 2.5 | 2.5 | 2.5 | 2.5 |
| 5. | ⟨O⟩(Cl)–C(Cl)=NOCOC₂H₅ | 2.5 | 2.5 | 2.5 | 2.5 | 2.5 |
| 6. | ⟨O⟩(Cl)–C(Cl)=NOCOCH₂Cl | 2.5 | 2.5 | 2.5 | 2.5 | 2.5 |
| 7. | Cl–⟨O⟩–C(Cl)=NOCOCH₃ | 2.5 | 2.5 | 2.5 | 2.5 | 2.5 |
| 8. | Cl–⟨O⟩(Cl)–C(Cl)=NOCOCH₃ | 2.5 | 2.5 | 2.5 | 2.5 | 2.5 |
| 9. | Cl,Cl–⟨O⟩(Cl)–C(Cl)=NOCOCH₃ | 2.5 | 2.5 | 5 | 2.5 | 2.5 |

-continued

| Compound | | Minimum Inhibitory Concentration (p.p.m.) Microorganisms | | | | |
|---|---|---|---|---|---|---|
| | | A.a | B.s | A.v | A.n | Y |
| 10. | [structure: 3-NO₂-phenyl-C(Cl)=NOCOCH₃] | 10 | 2.5 | 10 | 5 | 2.5 |
| 11. | [structure: 3-NO₂-phenyl-C(Cl)=NOCOC₂H₅] | 10 | 5 | 10 | 5 | 5 |
| 12. | [structure: 3-NO₂-phenyl-C(Cl)=NOCOCH₂Cl] | 10 | 5 | 10 | 10 | 5 |
| 13. | [structure: CH₃-phenyl-C(Cl)=NOCOCH₃] | 2.5 | 2.5 | 2.5 | 2.5 | 2.5 |
| 14. | [structure: CH₃-phenyl-C(Cl)=NOCOC₂H₅] | 2.5 | 5 | 2.5 | 2.5 | 2.5 |
| 15. | [structure: CH₃-phenyl-C(Cl)=NOCOCH₂Cl] | 5 | 2.5 | 2.5 | 2.5 | 2.5 |
| 16. | [structure: (CH₃)₂CH-phenyl-C(Cl)=NOCOCH₃] | 10 | 2.5 | 10 | 2.5 | 2.5 |
| 17. | [structure: (CH₃)₂CH-phenyl-C(Cl)=NOCOC₂H₅] | 20 | 2.5 | 10 | 2.5 | 2.5 |
| 18. | [structure: CH₃O-phenyl-C(Cl)=NOCOCH₃] | 20 | 2.5 | 20 | 2.5 | 2.5 |
| 19. | [structure: CH₃O-phenyl-C(Cl)=NOCOC₂H₅] | 20 | 2.5 | 10 | 20 | 5 |
| 20. | [structure: 3,5-Br₂-4-CH₃COO-phenyl-C(Cl)=NOCOCH₃] | 10 | 2.5 | 10 | 20 | 2.5 |
| 21. | [structure: 3,5-Br₂-4-C₂H₅COO-phenyl-C(Cl)=NOCOC₂H₅] | 20 | 2.5 | 10 | 20 | 5 |
| 22. | [structure: (CH₃)₂N-phenyl-C(Cl)=NOCOCH₃] | 10 | 5 | 10 | 40 | 5 |
| 23. | [structure: (CH₃)₂N-phenyl-C(Cl)=NOCOC₂H₅] | 10 | 10 | 10 | 40 | 5 |
| 24. | none | + | + | + | + | + |

+ free microorganism growth.

As shown in the above table, the slime control agents of this invention generally show strong activity inhibiting the growth of the microorganisms separated from the slime or white liquor in pulp and paper mill processes, and thus they inhibit the slime problem caused by these microorganisms.

The compounds recited in the present invention possess a killing and inhibiting activity against microorganisms. The above activities are distinguishable from each other, i.e., whether the compounds have a microbiocidal activity or have only a growth inhibitory activity not leading to the death of microorganisms.

The species and the amounts of microorganisms generated and bred during manufacturing paper and pulp vary depending upon the location of the paper or pulp mill and also the season, and in the case of using the slime control agents of this invention by adding them to circulating water in paper or pulp mill processes for inhibiting the growth of the microorganisms, it is desirable that the concentration of the effective component in the circulating water be maintained at about 2.5 to about 40 p.p.m., preferably above 2.5 to 20 p.p.m., but in most cases a lower concentration, e.g., about 2.5 to 10 p.p.m., gives a sufficient effect.

The α-chloro-o-acylbenzaldoxime derivatives used in the present invention are slightly soluble in water and, therefore, it is convenient to use the compounds previously dissolved in organic solvents, e.g., solutions having a concentration of 1 to 50 %, preferably 10 to 30 % by weight of the derivatives. Examples of the organic solvents suitable for this purpose are glycol ethers such as diethylene glycol monomethyl ether, alkylated phenyls such as trimethyl benzene, dimethylformamide, xylene and the like.

The dispersibility of organic solvent solutions of these compounds in the pulp or paper processing liquid can be increased by incorporating various emulsifiers or other surface active agents into the organic solution of the slime inhibitors of the present invention. Though any type of emulsifier commonly used in preparing oil-in-water or water-in-oil emulsions can be used in the present invention, nonionic type emulsifiers are generally most suitable in the present invention because of their excellent compatibility with the solution of the slime inhibitors in organic solvents recited above.

The α-chloro-o-acylbenzaldoxime derivatives per se exhibit an excellent slime inhibiting activty. These compounds may also be used in combination with other conventionally used slime inhibitors to obtain an improved activity. Specific examples of well-known slime inhibitors which can be used in conjunction with the α-chloro-benzaldoxime derivatives of this invention are halogenated phenols, methylenebisthiocyanate, and the like. For example, the halogenated phenols and methylenebisthiocyanate can be used in a ratio of from 0.5 to 2 parts by weight and 0.1 to 1 part by weight, respectively, per 1 part by weight of the α-chloro-o-acylbenzaldoxime derivatives.

The invention will now be further illustrated in detail by the following examples, but it should be understood that the additives and the compounds illustrated in the examples are shown merely for purpose of illustrating preferred embodiments, and they are not to be construed as limitative. In the examples, all percentages are given by weight.

EXAMPLE 1

An emulsion type slime inhibitor of this invention was prepared by emulsifying 25% α-chloro-o-acetyl-benzaldoxime in a mixture of 45% dimethylformamide and 25% xylene using 5% emulsifying agent. "Soruporu" 800A (trade name, made by Toho Kagaku Kogyo K.K.; a mixture of a polyoxethylene alkylallyl ether and a polyoxyethylene sorbitan alkylate).

EXAMPLE 2

An emulsion type slime inhibitor was prepared by emulsifying 20% α-chloro-o-acetyl-p-chlorobenzaldoxime in a mixture of 50% dimethylformamide and 25% diethylene glycol monomethyl ether using 5% emulsifying agent, "Soruporu" 800A (trade name, made by Toho Kagaku Kogyo K.K.).

EXAMPLE 3

An emulsion type slime inhibitor was prepared by emulsifying 10% α-chloro-o-acetyl-m-nitrobenzaldoxime and 5% methylene bisthiocyanate in a mixture of 50% dimethylformamide and 30% xylene using 5% emulsifying agent, "Soruporu" 800A (trade name, made by Toho Kagaku Kogyo K.K.).

EXAMPLE 4

An emulsion type slime inhibitor was prepared by emulsifying 20% α-chloro-o-acetyl-p-methylbenzaldoxime in a mixture of 30% dimethylformamide and 45% 1,2,4-trimethylbenzene using 5% emulsifying agent, "Soruporu" 800A (trade name, made by Toho Kagaku Kogyo K.K.).

EXAMPLE 5

An emulsion type slime inhibitor was prepared by emulsifying 20% α-chloro-o-acetyl-p-isopropylbenzaldoxime in a mixture of 45% 1,2,4-trimethylbenzene and 30% dimethylformamide using 5% emulsifying agent, "Soruporu" 800A (trade name, made by Toho Kagaku Kogyo K.K.).

EXAMPLE 6

The slime inhibitor prepared in Example 1 was added to a pulp mixture in a mixing chest of a paper manufacturing machine over a period of 8 hours per day so that the concentration of α-chloro-o-acetylbenzaldoxime in the mixture reached 5 p.p.m. and the amount of slime attached to a slime board suspended in the chest was measured. After a continuous run for two weeks, 5.3 g./30 cm.$^2$ of slime (dry amount) was attached to the slime board in the case of adding no slime inhibitor of this invention but substantially no slime was observed on the slime board in the case of adding the slime inhibitor of this invention.

EXAMPLE 7

The slime inhibitor prepared in Example 2 was added to a pulp mixture in a mixing chest of a machine for manufacturing newspaper over a period of 8 hours per day so that the concentration of the effective component in the mixture was 5 p.p.m. The paper tearing happens during the manufacturing of the paper and was compared with the case where no slime inhibitor was added to the pulp mixture.

In paper mill systems, slime deposits are generally carried to the paper forming sections thereby yielding unsightly blemishes which would result in breaks in the paper formed and consequently work stoppage.

After a continuous run for one week, the number of paper tearings caused by the formation of slime was about 9 per day in the case of adding no slime inhibitor, while the number of paper tearings was less than 2 under the same operation conditions in the case of adding the slime inhibitor of this invention. Working efficiency was thus increased in the latter case.

Moreover, after the end of the continuous run of the paper manufacturing operation the amount of the slime attached to the chest was much less in the case of adding the slime inhibitor of this invention than in the case of employing no slime inhibitor.

EXAMPLE 8

The slime inhibitor prepared in Example 4 was added to a pulp mixture in a mixing chest of a paper manufacturing machine over a period of eight hours per day so that the concentration of the effective component in the mixture was 5 p.p.m. and the amount of slime attached to a slime board suspended in the chest during the paper manufacturing operation was measured.

After a continuous run for two weeks, the amount of slime attached to the slime board was 5.5 g./30 cm.$^2$ (dry weight) in the case of adding no slime inhibitor, while substantially no slime was observed on the slime board in the case of adding the slime inhibitor of this invention.

EXAMPLE 9

The slime inhibitor prepared in Example 5 was added to a pulp mixture in a mixing chest of a machine for manufacturing newspaper over a period of eight hours per day so that the concentration of the effective component in the mixture was 5 p.p.m. and the state of paper tearing during the operation was compared with the case of adding no such slime inhibitor.

During a continuous run for one week the number of paper tearings was about 10 per day in the case of adding no slime inhibitor, while the number was less than 2 under the same conditions in the case of adding the slime inhibitor of this invention. Working efficiency was thus increased in the latter case. Moreover, the amount of slime attached to the chest after the end of the continuous run was less in the case of adding the slime inhibitor of this invention than in the case of adding no slime inhibitor.

From the above results, it will be understood that the α-chloro-o-acylbenzaldoxime derivatives of this invention have a strong fungicidal activity on microorganisms.

PREPARATION OF THE COMPOUNDS

The α-chloro-o-acylbenzaldoxime derivatives used in the present invention can be prepared by well known processes such as those disclosed in J. Am. C. S., Vol. 79, 462 (1957) and J. O. C., Vol. 25, 546 (1960). These processes generally comprise first preparing α-chloro-benzaldoximes from the corresponding benzaldoximes by chlorination, e.g., by bubbling a chlorinating agent such as chlorine gas into a solution of a starting benzaldoxime in a solvent such as hydrochloric acid or chloroform at a temperature of from about 5° to about 15°C, and then acylating the resulting α-chlorobenzaldoxime by well known procedures using an acid anhydride or an acid chloride, such as acetic anhydride, chloroacetyl chloride, etc., as an acylating agent corresponding to the —COR group in the α-chloro-o-acylbenzaldoximes of this invention. The acylation can generally be carried out by heating a mixture of α-chloro-benzaldoxime starting material and an equimolar to an excess amount of an acylating agent in an organic solvent such as benzene at an elevated temperature, e.g., from about 80° to about 90°C, for about 1 to about 3 hours. The preparation of the specific α-chloro-o-acylbenzaldoximes are illustrated below in greater detail.

EXAMPLE 10

A. Preparation of α-Chlorobenzaldoxime 60.5 g (0.5 mol) of benzaldoxime was suspended in 390 ml of 8N hydrochloric acid and chlorine gas was bubbled into the suspension while stirring and maintaining the reaction temperature at from 5° to 15°C. The oxime immediately showed a green color upon reaction with chlorine and, after allowing the reaction mixture to stand, pale yellow crystals of α-chlorobenzaldoxime precipitated. Filtration of the reaction mixture yielded 66 g of crystals having a melting point of 45°–47°C. Yield, about 84%.

B. Preparation of α-Chloro-o-Acylbenzaldoxime 77.8 g (0.5 mol) of α-chlorobenzaldoxime prepared above was dissolved in 300 ml of benzene and 61.8 g (0.6 mol) of acetic anhydride was added to the solution followed by heating for about 2 hours at a temperature from 80° to 90°C. The reaction mixture was then washed with water to remove acetic acid formed during the reaction, and then dried over anhydrous sodium sulfate. The benzene was removed from the reaction mixture by distillation under reduced pressure and the resulting concentrate was cooled to precipitate the desired product as crystals having a melting point of 38°–42°C. Recrystallization of the product from hydrated methanol yielded 59 g of white crystals having a melting point of 43°–45°C. Yield, about 60%.

EXAMPLE 11

A. Preparation of α-Chloro-3-Nitrobenzaldoxime 32.9 g (0.2 mol) of 3-nitrobenzaldoxime was suspended in 150 g of chloroform and chlorine gas was bubbled into the suspension while maintaining the reaction mixture at a temperature of from 5° to 10°C. 3-Nitrobenzaldoxime went into solution showing a green color upon reaction with chlorine to give a reaction mixture having a deep green color. The reaction mixture turned a pale yellowish-brown upon standing; chloroform was then removed from the reaction mixture under reduced pressure to give 37.6 g of pale yellow crystals having a melting point of 98°–101°C. Yield, 94%.

B. Preparation of α-Chloro-O-Chloroacetyl-3-Nitrobenzoldoxime 20 g (0.1 mol) of α-chloro-3-nitrobenzaldoxime prepared above was dissolved in 100 ml of benzene and to the solution was added 12.4 g (0.11 mol) of chloroacetyl chloride followed by heating for about 2 hours at a temperature of 80°C. After completion of the reaction, the reaction mixture was washed with water and dried over anhydrous sodium sulfate. Benzene was removed by distillation under reduced pressure to give crystals having a melting point of 48°–53°C. Recrystallization from hydrated methanol yielded 19.8 g of the desired compound as crystals having a melting point of 53°–55°C. Yield, 72%.

EXAMPLE 12

A. Preparation of α-Chloro-4-Chlorobenzaldoxime 31 g (0.2 mol) of 4-chlorobenzaldoxime was suspended in 200 g of chloroform and chlorine gas was bubbled through the suspension while maintaining the reaction mixture at a temperature of from 5° to 10°C. 3-Chlorobenzaldoxime went into solution while showing a green color upon reaction with chlorine to give a reaction mixture having a deep green color. The reaction mixture turned pale yellowish-brown upon standing; chloroform was then removed from the reaction mixture by distillation under reduced pressure to give 36 g of pale yellowish-brown crystals having a melting point of 75°–80°C. Yield, about 95%.

Recrystallization from ligroin yielded the desired compound as white crystals having a melting point of 86°–87°C.

B. Preparation of α-Chloro-O-Acetyl-4-Chlorobenzaldoxime

To 19 g (0.1 mol) of α-chloro-4-chlorobenzaldoxime prepared above was added 20.6 g (2.0 mol) of acetic anhydride followed by heating on a water bath at a temperature of from 80° to 90°C for about 2 hours. After completion of the reaction, the reaction mixture was poured into water to give pale yellow crystals. The product thus obtained was filtered, dried and recrystallized from ligroin to give 18 g of the desired product as white crystals having a melting point of 76°–77°C. Yield, 77%.

EXAMPLE 13

A. Preparation of α-Chloro-4-Methylbenzaldoxime 27 g (0.2 mol) of 4-methylbenzaldoxime was chlorinated in the same manner as described in Example 9 (A) in 150 ml of 8N hydrochloric acid to give 28 g of the product as white crystals having a melting point of 60°–70°C. Yield, about 82%.

B. Preparation of α-Chloro-O-Propionyl-4-Methylbenzaldoxime 17 g (0.1 mol) of α-chloro-4-methylbenzaldoxime prepared above was dissolved in 100 ml of benzene and 14.6 g (0.11 mol) of propionic anhydride was added to the solution followed by heating at a temperature of from 80° to 90°C. After completion of the reaction, the reaction mixture was washed with water and dried over anhydrous sodium sulfate. Benzene was removed by distillation under reduced pressure and the resulting concentrate was distilled using a vacuum pump to give 19 g of the desired compound as a liquid having a boiling point of 118° – 120°C/10 mm Hg. Yield, 84%.

While the invention has been described in detail and with reference to specific embodiments thereof, it will be apparent to one skilled in the art that various changes and modifications can be made therein without departing from the spirit and scope thereof.

What is claimed is:

1. A slime control composition for paper and pulp manufacturing comprising an organic solvent selected from the group consisting of diethylene glycol monomethyl ether, trimethyl benzene, dimethylformamide, and xylene and as an effective component in said composition about 2.5 to about 40 parts per million of an α-chloro-o-acylbenzaldoxime derivative represented by the formula

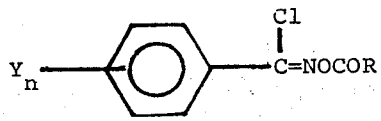

wherein Y represents chlorine, nitro, methyl, isopropyl, methoxy, dimethylamino, propionyloxy or acetoxy; R represents methyl, ethyl or monochloromethyl; and n represents 0 or an integer of 1–3.

2. The slime control composition as claimed in claim 1 in concentrate form where the concentration of α-chloro-o-acylbenzaldoxime derivative in the solvent is from 1 to 50% by weight.

3. The slime control composition as claimed in claim 2, where the concentration is 10 to 30% by weight.

4. The composition of claim 1, wherein the α-chloro-o-acylbenzaldoxime is α-chloro-o-acetylbenzaldoxime

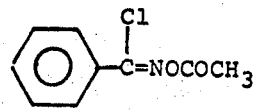

5. The composition of claim 1, wherein the α-chloro-o-acylbenzaldoxime is α-chloro-o-propionylbenzaldoxime

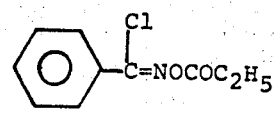

6. The composition of claim 1, wherein the α-chloro-o-acylbenzaldoxime is α-chloro-o-chloroacetylbenzaldoxime

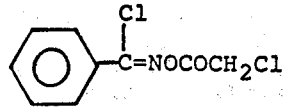

7. The composition of claim 1, wherein the α-chloro-o-acylbenzaldoxime is α-chloro-o-acetyl-2-chlorobenzaldoxime

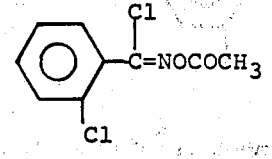

8. The composition of claim 1, wherein the α-chloro-o-acylbenzaldoxime is α-chloro-o-propionyl-2-chlorobenzaldoxime

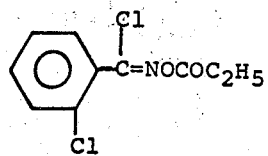

9. The composition of claim 1, wherein the α-chloro-o-acylbenzaldoxime is α-chloro-o-chloroacetyl-2-chlorobenzaldoxime

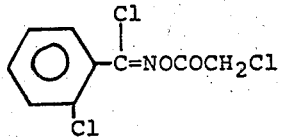

10. The composition of claim 1, wherein the α-chloro-o-acylbenzaldoxime is α-chloro-o-acetyl-4-chlorobenzaldoxime

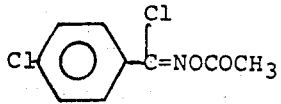

11. The composition of claim 1, wherein the α-chloro-o-acylbenzaldoxime is α-chloro-o-acetyl-2,4-dichlorobenzaldoxime

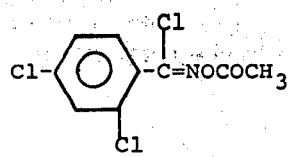

12. The composition of claim 1, wherein the α-chloro-o-acylbenzaldoxime is α-chloro-o-acetyl-2,6-dichlorobenzaldoxime

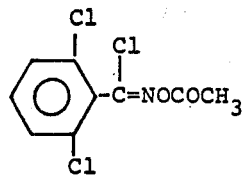

13. The composition of claim 1, wherein the α-chloro-o-acylbenzaldoxime is α-chloro-o-acetyl-3-nitrobenzaldoxime

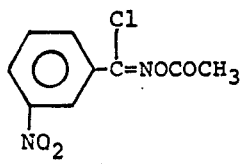

14. The composition of claim 1, wherein the α-chloro-o-acylbenzaldoxime is α-chloro-o-propionyl-3-nitrobenzaldoxime

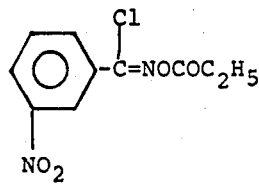

15. The composition of claim 1, wherein the α-chloro-o-acylbenzaldoxime is α-chloro-o-chloroacetyl-3-nitrobenzaldoxime

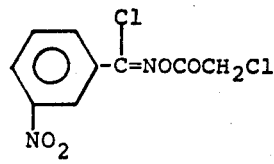

16. The composition of claim 1, wherein the α-chloro-o-acylbenzaldoxime is α-chloro-o-acetyl-4-methylbenzaldoxime

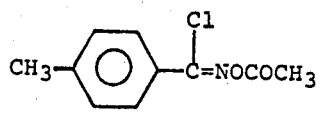

17. The composition of claim 1, wherein the α-chloro-o-acylbenzaldoxime is α-chloro-o-propionyl-4-methylbenzaldoxime

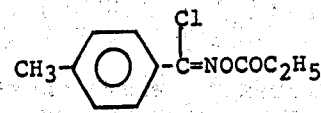

18. The composition of claim 1, wherein the α-chloro-o-acylbenzaldoxime is α-chloro-o-chloroacetyl-4-methylbenzaldoxime

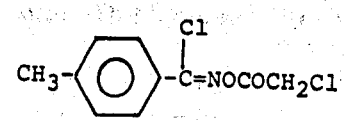

19. The composition of claim 1, wherein the α-chloro-o-acylbenzaldoxime is α-chloro-o-acetyl-4-isopropylbenzaldoxime

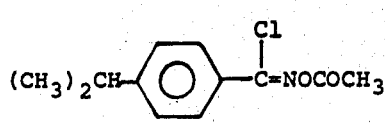

20. The composition of claim 1, wherein the α-chloro-o-acylbenzaldoxime is α-chloro-o-propionyl-4-isopropylbenzaldoxime

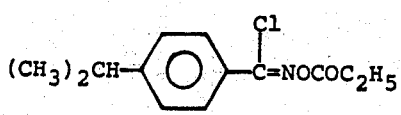

21. The composition of claim 1, wherein the α-chloro-o-acylbenzaldoxime is α-chloro-o-acetyl-4-methoxybenzaldoxime

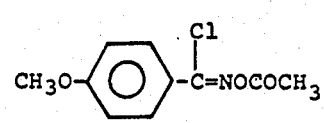

22. The composition of claim 1, wherein the α-chloro-o-acylbenzaldoxime is α-chloro-o-propionyl-4-methoxybenzaldoxime

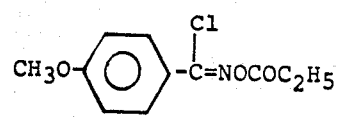

23. The composition of claim 1, wherein the α-chloro-o-acylbenzaldoxime is α-chloro-o-acetyl-4-dimethylaminobenzaldoxime

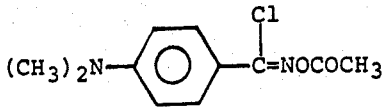

24. The composition of claim 1, wherein the α-chloro-o-acylbenzaldoxime is α-chloro-o-propionyl-4-dimethylaminobenzaldoxime

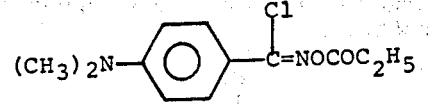

25. A slime control composition for paper and pulp manufacturing comprising an organic solvent selected from the group consisting of diethylene glycol monomethyl ether, trimethyl benzene, dimethylformamide, and xylene and as an effective component in said composition about 2.5 to about 40 parts per million of α-chloro-o-acetyl-4-acetoxy-3,5-dibromobenzaldoxime

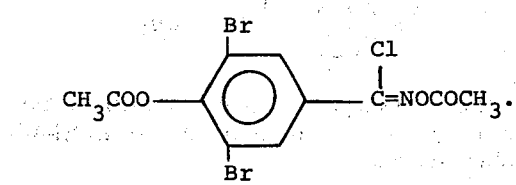

26. A slime control composition for paper and pulp manufacturing comprising an organic solvent selected from the group consisting of diethylene glycol monomethyl ether, trimethyl benzene, dimethylformamide, and xylene and as an effective component in said composition about 2.5 to about 40 parts per million of α-chloro-o-propionyl-4-propionyloxy-3,5-dibromobenzaldoxime

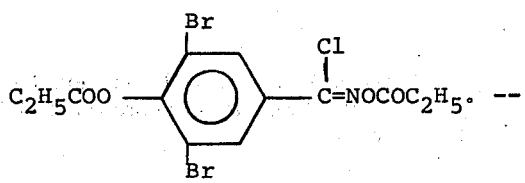

* * * * *